(12) United States Patent
Stanley, II

(10) Patent No.: US 11,051,872 B2
(45) Date of Patent: Jul. 6, 2021

(54) ELECTROSURGICAL ELECTRODES AND SYSTEMS AND METHODS INCLUDING SAME

(71) Applicant: Robert James Stanley, II, Cary, NC (US)

(72) Inventor: Robert James Stanley, II, Cary, NC (US)

(73) Assignee: Robert James Stanley, II, Cary, NC (US)

( * ) Notice: Subject to any disclaimer, the term of this patent is extended or adjusted under 35 U.S.C. 154(b) by 884 days.

(21) Appl. No.: 15/830,863

(22) Filed: Dec. 4, 2017

(65) Prior Publication Data

US 2019/0167340 A1    Jun. 6, 2019

(51) Int. Cl.
| | |
|---|---|
| *A61B 18/14* | (2006.01) |
| *A61B 90/70* | (2016.01) |
| *A61C 3/00* | (2006.01) |
| *A61B 18/00* | (2006.01) |

(52) U.S. Cl.
CPC .......... *A61B 18/1402* (2013.01); *A61B 90/70* (2016.02); *A61B 2018/0047* (2013.01); *A61B 2018/00321* (2013.01); *A61B 2018/00577* (2013.01); *A61B 2018/00625* (2013.01); *A61B 2018/00976* (2013.01); *A61B 2018/1407* (2013.01); *A61C 3/00* (2013.01)

(58) Field of Classification Search
CPC ...... A61B 18/1402; A61B 2018/00625; A61B 2018/00577; A61B 2018/00976; A61B 2018/0097; A61B 2018/1407; A61B 2018/00321
See application file for complete search history.

(56) References Cited

U.S. PATENT DOCUMENTS

| | | | |
|---|---|---|---|
| 3,730,188 A | 5/1973 | Ellman | |
| 4,221,222 A | 9/1980 | Detsch | |
| 4,449,926 A | 5/1984 | Weiss | |
| 4,657,016 A | 4/1987 | Garito et al. | |
| 4,754,754 A | 7/1988 | Garito et al. | |
| 5,630,812 A | 5/1997 | Ellman et al. | |
| 5,683,387 A | 11/1997 | Garito et al. | |
| 5,733,283 A | 3/1998 | Malis et al. | |
| 5,746,746 A | 5/1998 | Garito et al. | |
| 5,810,764 A * | 9/1998 | Eggers ............... | A61B 18/1206 604/23 |

(Continued)

OTHER PUBLICATIONS

International Search Report and Written Opinion of the International Searching Authority, International Application No. PCT/US2017/067260, dated Aug. 30, 2018, 9 pp.

(Continued)

*Primary Examiner* — Linda C Dvorak
*Assistant Examiner* — Ryan T Clark
(74) *Attorney, Agent, or Firm* — Myers Bigel, P.A.

(57) ABSTRACT

A method for treating surface tissue of a patient includes: providing an electrode having a contact surface, wherein the contact surface has a curved profile; placing the contact surface in contact with surface tissue of the patient; and sliding the contact surface across and in contact with the surface tissue while applying electrosurgical currents to the surface tissue via the contact surface to thereby vaporize and ablate the surface tissue and form a treated band of the surface tissue.

16 Claims, 6 Drawing Sheets

(56) References Cited

U.S. PATENT DOCUMENTS

| | | | |
|---|---|---|---|
| 5,913,864 A | 6/1999 | Garito et al. | |
| 5,954,686 A | 9/1999 | Garito et al. | |
| 5,984,918 A | 11/1999 | Garito et al. | |
| 6,071,281 A * | 6/2000 | Burnside | A61B 18/1482 606/37 |
| D441,077 S | 4/2001 | Garito et al. | |
| 6,231,571 B1 | 5/2001 | Ellman et al. | |
| 6,238,388 B1 | 5/2001 | Ellman et al. | |
| D453,222 S | 1/2002 | Garito et al. | |
| 6,387,093 B1 | 5/2002 | Ellman et al. | |
| 6,409,726 B1 | 6/2002 | Ellman et al. | |
| 6,416,512 B1 | 7/2002 | Ellman et al. | |
| 6,447,510 B1 | 9/2002 | Ellman et al. | |
| 6,562,036 B1 | 5/2003 | Ellman et al. | |
| 6,572,613 B1 | 6/2003 | Ellman et al. | |
| 6,610,057 B1 | 8/2003 | Ellman et al. | |
| 6,673,072 B1 | 1/2004 | Garito et al. | |
| 6,926,717 B1 | 8/2005 | Garito et al. | |
| 7,094,231 B1 | 8/2006 | Ellman et al. | |
| 7,160,295 B1 | 1/2007 | Garito et al. | |
| 7,507,232 B1 | 3/2009 | Garito et al. | |
| 7,621,744 B2 | 11/2009 | Massoud | |
| 7,879,032 B1 | 2/2011 | Garito et al. | |
| 7,935,110 B1 | 5/2011 | Garito et al. | |
| 2003/0130653 A1 | 7/2003 | Sixto et al. | |
| 2004/0034339 A1 | 2/2004 | Stoller et al. | |
| 2004/0236203 A1 | 11/2004 | Salvo | |
| 2007/0055226 A1 | 3/2007 | Garito et al. | |
| 2008/0294160 A1 | 11/2008 | Garito et al. | |
| 2009/0069802 A1 | 3/2009 | Garito et al. | |
| 2009/0176188 A1 * | 7/2009 | Tobis | A61C 3/02 433/102 |
| 2013/0345620 A1 | 12/2013 | Zemel et al. | |
| 2014/0214021 A1 | 7/2014 | Varney | |
| 2015/0034122 A1 * | 2/2015 | Mottola | A61B 90/70 134/6 |
| 2016/0228177 A1 | 8/2016 | Eckhouse et al. | |
| 2016/0256675 A1 | 9/2016 | Slayton | |
| 2017/0319255 A1 | 11/2017 | Cosmescu | |
| 2017/0354476 A1 | 12/2017 | Vasan et al. | |
| 2018/0193083 A1 | 7/2018 | Bannino | |

OTHER PUBLICATIONS

Alasmari, Dhafer S. "An insight into gingival depigmentation techniques: The pros and cons" Int J Health Sci 12(5):84-89 (2018).
Arava-Parastatidis et al. "Multifocal pigmentation of the oral cavity" J Am Dent Assoc 142(1):53-56 (Jan. 2011).
Bashetty et al. "Electrosurgery in aesthetic and restorative dentistry: A literature review and case reports" J Conserv Dent 12(4):139-144 (2009).
Bhatia et al. "Assessment of the width of attached gingiva using different methods in various age groups: A clinical study" J Indian Soc Periodontal 19(2):199-202 (2015).
çiçek et al. "The normal and pathological pigmentation of oral mucous membrane: a review" J Contemp Dent Pract 4:76-86 (Aug. 15, 2003).
Dummett, Clifton O. "Physiologic pigmentation of the oral and cutaneous tissues in the Negro" J Dent Res 25:421-432 (1946).
Hassona et al. "Prevalence and clinical features of pigmented oral lesions" Int J Dermatol 55(9):1005-1013 (Sep. 2016).
Kathariva et al. "Split mouth de-epithelization techniques for gingival depigmentation: a case series and review of literature" J Indian Soc Periodontal 15(2):161-168 (2011).
Kaur et al. "Duration of reappearance of gingival melanin pigmentation after surgical removal—a clinical study" J Indian Soc Periodontal 14(2):101-105 (2010).
Kippenberger et al. "Melanocytes in vitro: how do they undergo mitosis?" Pigment Cell Res 10:85-87 (Jan. 27, 1997).
Mahesh et al. "Gingival pigmentation reduction: a novel therapeutic modalit" J Cutan Aesthet Surg 5(2):137-140 (2012).
Maness et al. "Histologic evaluation of electrosurgery with varying frequency and waveform" J Prosthet Dent 40(3):304-308 (Sep. 1978).
Moneim et al. "Gingival pigmentation (cause, treatment and histological preview)" Future Dental Journal 3:1-7 (2017).
Müller et al. "Thickness of masticatory mucosa" J Clin Periodontal 27:431-436 (2000).
Müller, Susan "Melanin-associated pigmented lesions of the oral mucosa: presentation, differential diagnosis, and treatment" Dermatol Ther 23:220-229 (2010).
Murthy et al. "Treatment of gingival hyperpigmentation with rotary abrasive, scalpel, and laser techniques: A case series" J Indian Soc Periodontal 16:614-619 (2012).
Muruppel et al. "Laser-assisted depigmentation—an introspection of the science, techniques, and perceptions" Dent J 8:88 (2020).
Negi et al. "Ceramic soft tissue trimming bur: A new tool for gingival depigmentation" J Oral Biol Craniofac Res 9:14-18 (2019).
Perlmutter et al. "Repigmentation of the gingiva following surgical injury" J Periodontal 57(1):48-50 (Jan. 1986).
Shah et al. "Prevalence of gingival biotype and its relationship to clinical parameters" Contemp Clin Dent 6(Suppl 1):S167-171 (2015).
Sharma et al. "Radiosurgery in dentistry: a brief review" Annals of Dental Research 2(1):8-21 (Jun. 2012).
Thangavelu et al. "Pink esthetics in periodontics—Gingival depigmentation: A case series" J Pharm Bioallied Sci 4(S2-1):S186-S190 (Aug. 2012).
Thayath et al. "Surgical management of gingiva to restore aesthetics and function of the oral cavity—a comprehensive review" Int. J Contemp Dent 5:28-33 (Jun. 2014).
Turner et al. "Analysis of tissue margins of cone biopsy specimens obtained with "cold knife," CO2 and Nd:YAG lasers and a radiofrequency surgical unit" J Reprod Med 37:607-610 (1992).
Verma et al. "Gingival depigmentation" Indian Journal of Clinical Practice 23(12):801-803 (May 2013).

* cited by examiner

ELECTROSURGICAL ELECTRODES AND SYSTEMS AND METHODS INCLUDING SAME

FIELD OF THE INVENTION

The present invention relates to electrosurgical apparatus and methods and, more particularly, to electrosurgical electrodes and electrosurgical apparatus and methods including the same.

BACKGROUND

Electrosurgery is a common procedure for dentists, doctors, and veterinarians. Electrosurgical handpieces are commercially available that will accommodate a wide variety of electrode shapes and sizes, such as needles, blades, scalpels, balls and wire loops. Also, multi-function electrodes are available.

The electrodes can be used in many surgical procedures in which a conventional scalpel is employed, mainly for general cutting procedures. An electrosurgical scalpel electrode has the advantage of providing electrosurgical currents at the sharp edge of the scalpel, which assist in cutting tissue while at the same time providing a coagulation effect. Another known shape is the ball electrode, which is a spherical ball on the end of an electrode shank used for coagulation.

While these various shaped electrodes are suitable for their intended purposes of cutting and coagulation, occasions arise from time to time when these electrodes are pressed into service to ablate tissue. In this situation, the known electrodes typically fall short of a desired outcome.

SUMMARY

According to embodiments of the invention, a method for treating surface tissue of a patient includes: providing an electrode having a contact surface, wherein the contact surface has a curved profile; placing the contact surface in contact with surface tissue of the patient; and sliding the contact surface across and in contact with the surface tissue while applying electrosurgical currents to the surface tissue via the contact surface to thereby vaporize and ablate the surface tissue and form a treated band of the surface tissue.

In some embodiments, the curved profile of the contact surface extends along a first axis, the contact surface has a linear profile along a second axis perpendicular to the first axis, and the step of sliding the contact surface across and in contact with the surface tissue includes sliding the contact surface across and in contact with the surface tissue in a direction substantially parallel to the first axis while applying electrosurgical currents to the surface tissue via the contact surface to thereby vaporize and ablate the surface tissue.

In some embodiments, the curved profile has a minimum arc radius of at least 1.5 mm.

According to some embodiments, the step of sliding the contact surface across and in contact with the surface tissue includes sliding the contact surface across and in contact with the surface tissue in a brushing direction while applying electrosurgical currents to the surface tissue via the contact surface to thereby vaporize and ablate the surface tissue, an engagement interface between the contact surface and the surface tissue defines a contact band having a first dimension parallel to the brushing direction and a second dimension perpendicular to the first dimension, and the second dimension is greater than the first dimension.

In some embodiments, the first dimension is in the range of from about 1 mm to 3 mm, and the second dimension is in the range of from about 1 mm to 4 mm.

In some embodiments, the step of sliding the contact surface across and in contact with the surface tissue includes ablating the surface tissue without cutting the surface tissue.

According to some embodiments, the electrode further includes a lateral edge, and the method further includes scraping residual tissue from the treated band using the lateral edge.

In some embodiments, the method further includes: mounting a wiping insert on the electrode; and wiping residual tissue from the treated band using the wiping insert.

In some embodiments, the electrode includes first and second opposed lateral edges, and the method includes monitoring the first lateral edge to determine a location of the second lateral edge relative to the patient.

In some embodiments, the electrode includes a bottom wall and a top wall overlying the bottom wall, the contact surface is on the bottom wall, the top wall includes a planar surface overlying the contact surface, and the method includes monitoring the planar surface to determine a depthwise location of the contact surface relative to the surface tissue.

According to some embodiments, the method includes: providing an electrode set including a plurality of electrodes having contact surfaces of different widths from one another, each of the electrodes having a curved profile; and selecting the electrode from the set of electrodes.

In some embodiments, the surface tissue is skin tissue.

In some embodiments, the surface tissue is gum tissue.

According to some embodiments, the method includes using the electrode to ablate the gum tissue to a depth in the range of from about 0.01 mm to 0.15 mm in the treated band.

In some embodiments, the method includes using the electrode to ablate an epithelium layer of the gum tissue while leaving an underlying connective tissue layer substantially undamaged in the treated band.

In some embodiments, the method is used to remove gingiva hyperplasia from the patient's gums.

In some embodiments, the method is used to remove racial pigmentation from the patient's gums.

According to some embodiments, the curved profile of the contact surface extends along a first axis, the contact surface has a linear profile along a second axis perpendicular to the first axis, and the step of sliding the contact surface across and in contact with the gum tissue includes sliding the contact surface across and in contact with the gum tissue in a direction substantially parallel to the first axis while applying electrosurgical currents to the gum tissue via the contact surface to thereby vaporize and ablate the gum tissue.

In some embodiments, the curved profile has a minimum arc radius of at least 1.5 mm.

According to some embodiments, the step of sliding the contact surface across and in contact with the gum tissue includes sliding the contact surface across and in contact with the gum tissue in a brushing direction while applying electrosurgical currents to the gum tissue via the contact surface to thereby vaporize and ablate the gum tissue, and an engagement interface between the contact surface and the gum tissue defines a contact band having a first dimension parallel to the brushing direction and a second dimension perpendicular to the first dimension, and the second dimension is greater than the first dimension.

In some embodiments, the first dimension is in the range of from about 0.5 mm to 2 mm, and the second dimension is in the range of from about 1 mm to 4 mm.

In some embodiments, the step of sliding the contact surface across and in contact with the gum tissue includes ablating the gum tissue without cutting the gum tissue.

In some embodiments, the electrode further includes a lateral edge, and the method further includes scraping residual tissue from the treated band using the lateral edge.

According to some embodiments, the method further includes: mounting a wiping insert on the electrode; and wiping residual tissue from the treated band using the wiping insert.

In some embodiments, the electrode includes first and second opposed lateral edges, and the method includes monitoring the first lateral edge to determine a location of the second lateral edge relative to the patient's gums.

In some embodiments, the electrode includes a bottom wall and a top wall overlying the bottom wall, the contact surface is on the bottom wall, the top wall includes a planar surface overlying the contact surface, and the method includes monitoring the planar surface to determine a depthwise location of the contact surface relative to the gum tissue.

According to some embodiments, an electrosurgical electrode for performing electrosurgery on a patient includes a bottom wall and a top wall overlying the bottom wall. The bottom wall includes a contact surface having a curved profile, The top wall includes a planar surface overlying the contact surface. The electrode is configured to enable a user to monitor the planar surface to determine a depthwise location of the contact surface relative to the patient.

According to some embodiments, an electrosurgical apparatus for performing electrosurgery on a patient includes an electrode and a wiping insert. The electrode includes a contact surface and a socket defined in the electrode. The wiping insert is removably mounted in the socket.

According to some embodiments, a method for performing electrosurgery on tissue of a patient tissue includes providing an electrosurgical apparatus including: an electrode including a contact surface and a socket defined in the electrode; and a wiping insert removably mounted in the socket. The method further includes: contacting the contact surface with the tissue while applying electrosurgical currents to the tissue via the contact surface to thereby electrosurgically treat the tissue; and thereafter wiping the tissue using the wiping insert in the socket.

According to some embodiments, an electrosurgical electrode for performing electrosurgery on a patient includes a contact surface. The contact surface that has a curved profile along a first axis, and a flat profile along a second axis perpendicular to the first axis. The curved profile has a minimum arc radius of at least 1.5 mm. A width of the contact surface in a dimension parallel to the second axis is at least 1 mm.

It is noted that aspects of the invention described with respect to one embodiment, may be incorporated in a different embodiment although not specifically described relative thereto. That is, all embodiments and/or features of any embodiment can be combined in any way and/or combination. These and other objects and/or aspects of the present invention are explained in detail in the specification set forth below.

BRIEF DRAWING DESCRIPTION

The accompanying figures are included to provide a further understanding of the present invention, and are incorporated in and constitute a part of this specification. The drawings illustrate some embodiments of the present invention and, together with the description, serve to explain principles of the present invention.

DETAILED DESCRIPTION OF EMBODIMENTS OF THE INVENTION

Figure 1:
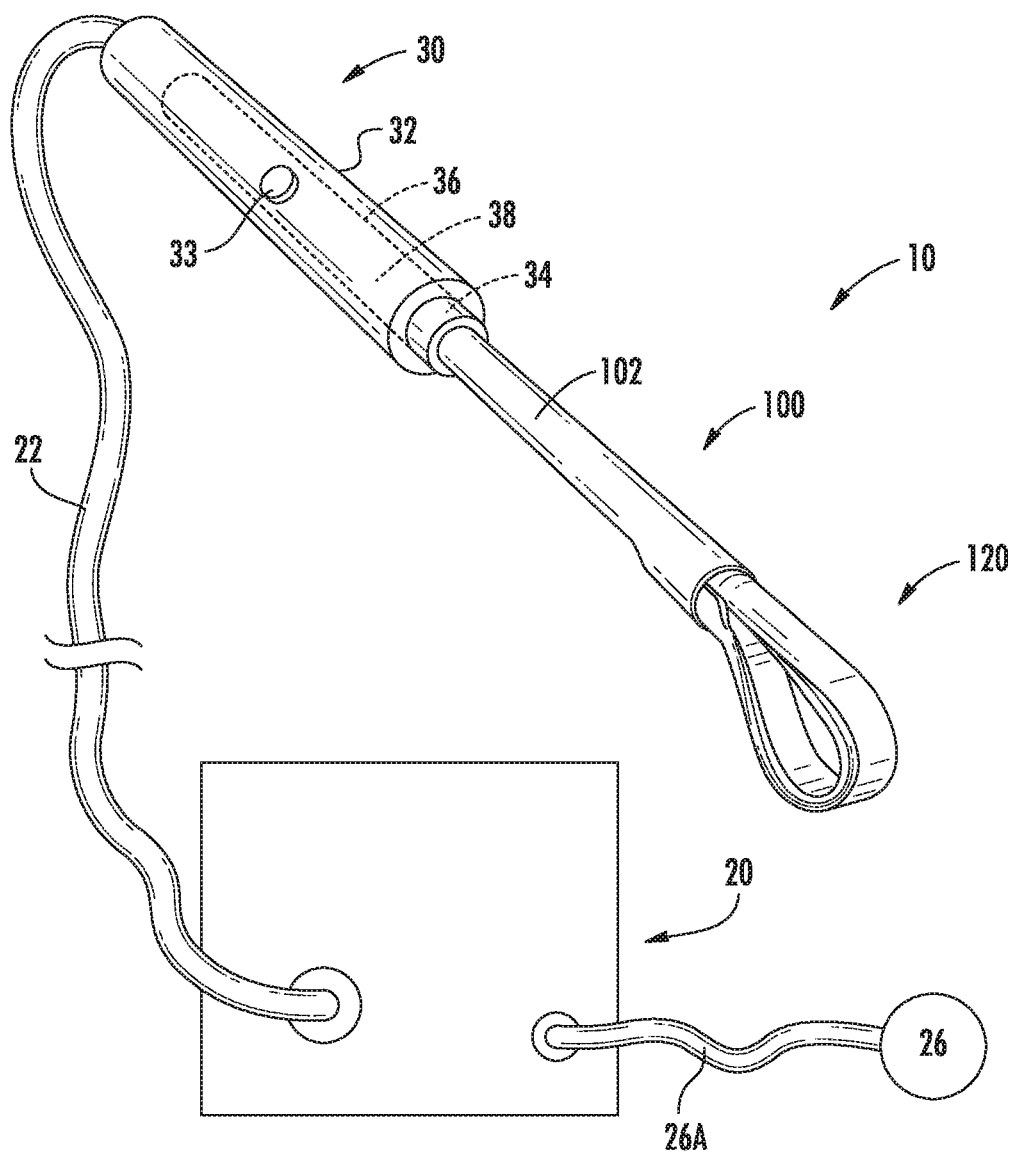
FIG. 1 is a schematic, perspective view of an electrosurgical system according to embodiments of the invention.

The present invention now will be described more fully hereinafter with reference to the accompanying drawings, in which illustrative embodiments of the invention are shown. In the drawings, the relative sizes of regions or features may be exaggerated for clarity. This invention may, however, be embodied in many different forms and should not be construed as limited to the embodiments set forth herein; rather, these embodiments are provided so that this disclosure will be thorough and complete, and will fully convey the scope of the invention to those skilled in the art.

It will be understood that when an element is referred to as being "coupled" or "connected" to another element, it can be directly coupled or connected to the other element or intervening elements may also be present. In contrast, when an element is referred to as being "directly coupled" or "directly connected" to another element, there are no intervening elements present. Like numbers refer to like elements throughout.

In addition, spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly.

Well-known functions or constructions may not be described in detail for brevity and/or clarity.

As used herein the expression "and/or" includes any and all combinations of one or more of the associated listed items.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, "monolithic" means an object that is a single, unitary piece formed or composed of a material without joints or seams.

As used herein, "operator" may include a physician, veterinarian, dentist or other clinician, for example. As used herein, "operator" may include two or more people in collaboration.

With reference to FIGS. 1-11, an electrosurgical system 10 according to some embodiments of the invention is shown therein. With reference to FIG. 1, the system 10 includes a brush electrode 100 according to some embodiments of the invention. The system 10 further includes an electrosurgical apparatus 20, a handpiece 30, and an electrically insulated electrical cable 22 operatively connecting the handpiece 20 to the electrosurgical apparatus 20.

In accordance with methods of the invention, the electrosurgical system 10 and the brush electrode 100 can be used to treat tissue of a patient. As discussed herein, the system 10 and the electrode 100 can be used to electrosurgically vaporize and thereby ablate tissue by contacting the electrode 100 with the tissue while applying RF current from the electrosurgical apparatus 20 to the tissue through the electrode 100. In some embodiments, an energized contact surface of the electrode is brushed or slid over a surface of exposed tissue such that the electrode contact surface ablates a treated band of the tissue. In some embodiments, the treated band is relatively broad and a substantially uniform depth of the tissue is ablated across the width of the treated band. In some embodiments, the ablated tissue is exposed surface tissue. In some embodiments, the ablated tissue is skin tissue. In some embodiments, the ablated tissue is gum tissue.

The electrode 100 may also be used to cut or scrape tissue without the application of the RF current. For example, the electrode 100 can be used to scrape away tissue that has been desiccated or coagulated by the aforementioned ablating step.

In some embodiments, the electrosurgical system 10 and the brush electrode 100 can also be used to electrosurgically cut, scrape, cauterize, coagulate, and/or desiccate tissue by contacting the electrode 100 with the tissue while applying RF current from the electrosurgical apparatus 20 to the tissue through the electrode 100.

The electrosurgical apparatus 20 may be any suitable electrosurgical apparatus. According to some embodiments, the electrosurgical apparatus 20 is a radiofrequency (RF) radiosurgical energy source operable to selectively generate and deliver alternating polarity electrical current (hereinafter, referred to as an RF generator). In some embodiments, the electrosurgical apparatus is an ultra-high frequency RF generator. Suitable electrosurgical RF generators may include the RADIOSURGE 3™ electrosurgical unit available from Ellman International, Inc. of Hewlett, N.Y. In some embodiments, the apparatus 20 provides current to the electrode 100 at a high operating frequency (in some embodiments, in the range of 2 to 4 MHz and, in some embodiments, about 3.8 MHz). The electrosurgical apparatus 20 may include one or more switches that enable an operator to selectively turn the supplied RF current on and off. For example, the apparatus 20 may include a switch 33 (e.g., a button switch) on the handpiece 30 and a redundant foot operable switch (not shown).

The system 10 may further include a dispersive electrode 26 operatively electrically connected to the electrosurgical unit 20 or to electrical ground by an electrical cable 26A. In use of the system 10, the dispersive electrode 26 is mounted on and in electrical contact with the patient's body and spaced apart from the surgical region. The dispersive electrode 26 operates to disperse the RF current and thereby prevent unintended injury to the tissue underlying the tissue intended to be treated using the electrode 100. The electric current oscillates between the electrode 100 and the dispersive electrode 26 with the patient interposed between the electrodes 100, 26.

The handpiece 30 includes a handle 32 and a locking mechanism 34 such as a collet. A bore 36 is located in the handle 32 and contains an electrical contact 38. The electrical contact 38 is electrically connected to the cable 22. The electrical contact 38 may be a tubular member.

Figure 2:
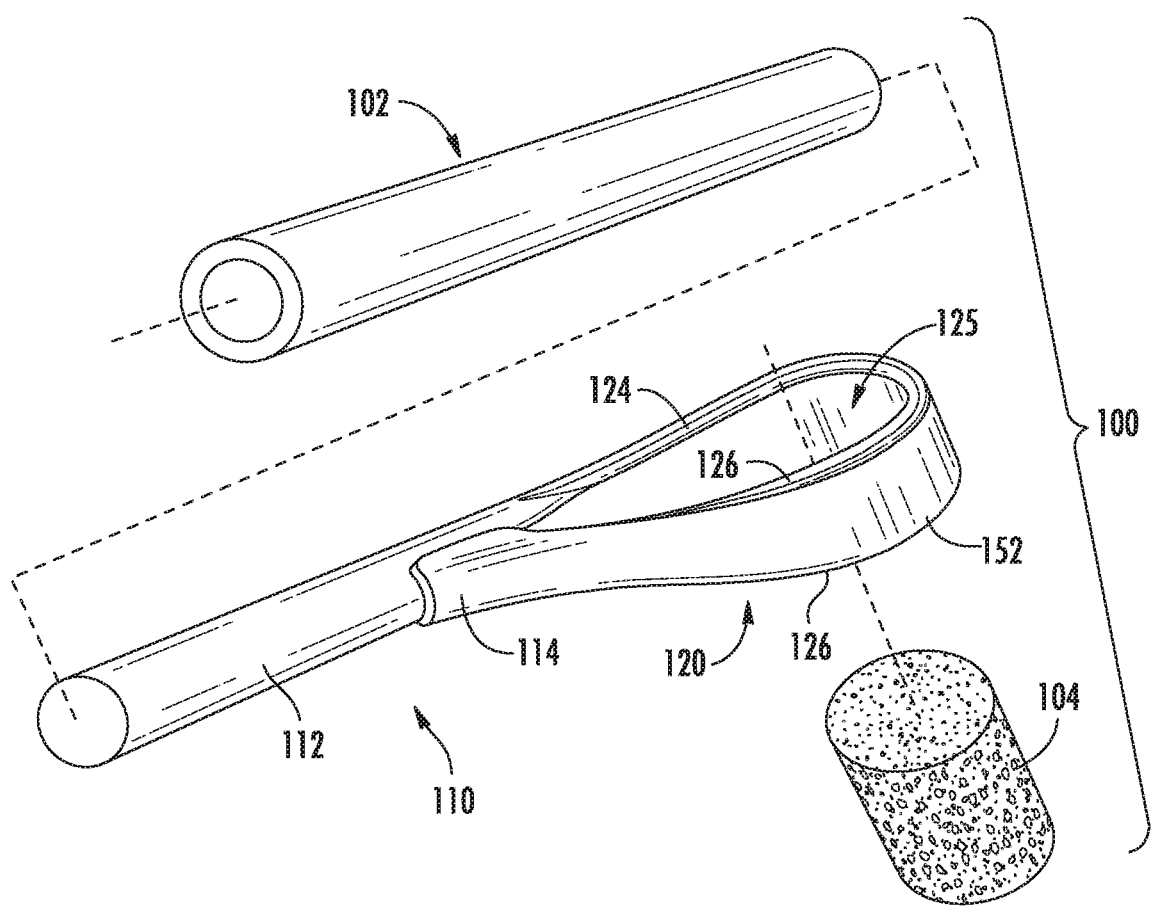
FIG. 2 is a fragmentary, exploded, perspective view of an electrode according to embodiments of the invention and forming a part of the system of FIG. 1.
Figure 3:
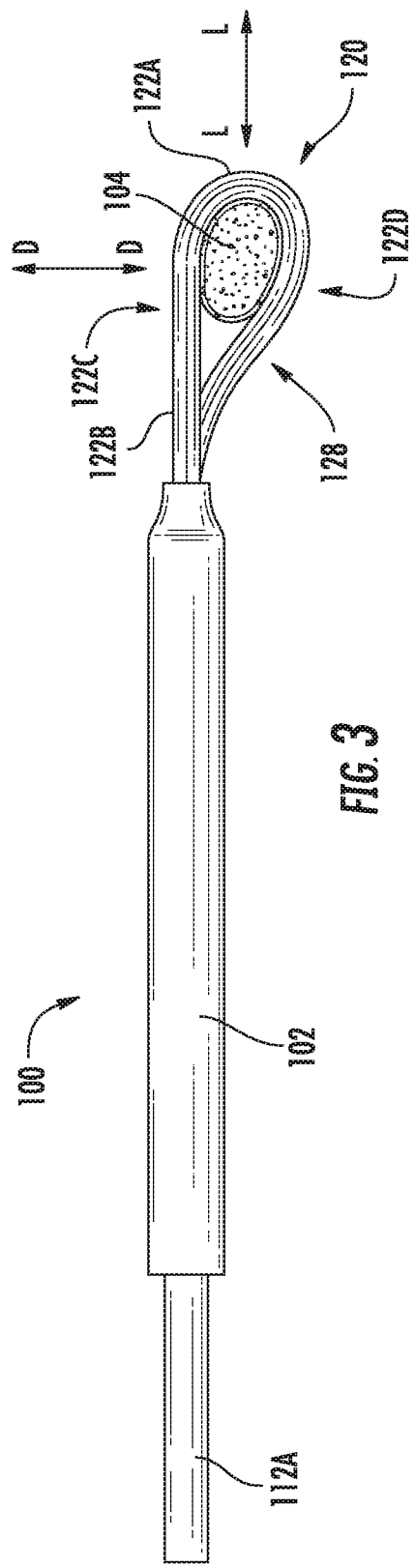
FIG. 3 is a side view of the electrode of FIG. 2.
Figure 4:
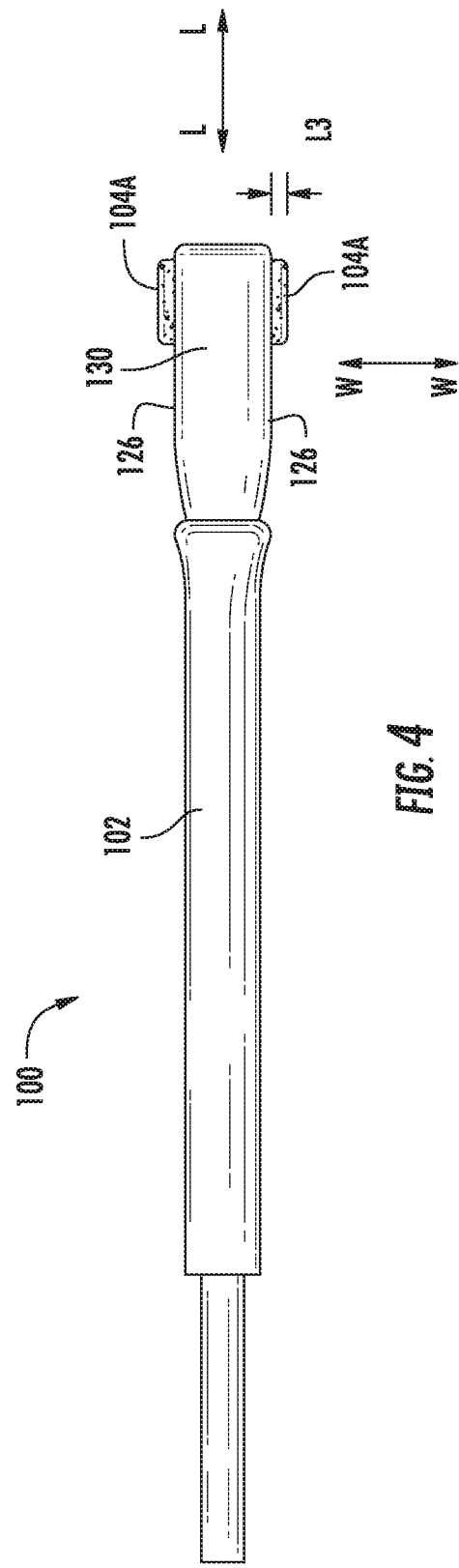
FIG. 4 is a top view of the electrode of FIG. 2.

The brush electrode 100 includes an electrode member 110 and an insulation sleeve 102. The electrode 100 may further include a supplemental wiping insert 104 (FIGS. 2-4). In some embodiments, the insert 104 is a pliable, absorbent member and, in some embodiments, is a sponge or gauze.

The electrode member 110 is formed of an electrically conductive material or materials. In some embodiments, the electrode member 110 is formed of metal. Suitable metals may include brass, or molybdenum. In some embodiments, the electrode member 110 is a unitary body. In some embodiments, the electrode member 110 is monolithic.

The insulation sleeve 102 is formed of an electrically insulating material or materials. The insulation sleeve 102 may be a preformed component or a coating. In some embodiments, the insulation sleeve 102 is formed of a polymeric insulating material. Suitable materials may include heat shrinkable thermoplastic. The insulation sleeve 102 surrounds a portion of the electrode member 110 to prevent the electrode 100 from inadvertently burning the patient.

The electrode member 110 includes a shank 112, a working portion (or active end portion) 120, and a tail portion 114. The shank 112 is a straight rod disposed in the insulation sleeve 102, except for a connector portion 112A that extends proximally from the insulation sleeve 102. The shank 112 may have an outer diameter of about 1/16 inch.

In use, the electrode 100 is inserted into the bore 36 of the handpiece to electrically connect the working portion 120 to the contact 38. The contact 38 is in turn electrically connected to the apparatus 20 via the cable 22. The insulation sleeve 102 electrically insulates the portion of the electrode member 110 extending between the handpiece 30 and the working end 120.

Figure 5:
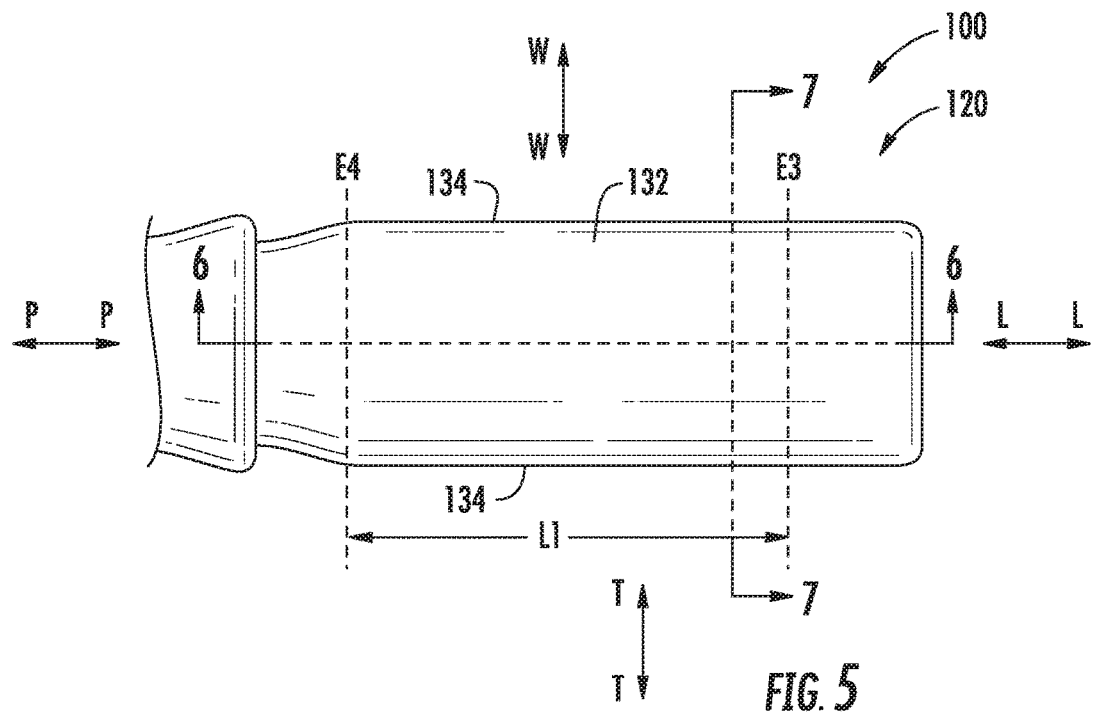
FIG. 5 is an enlarged, fragmentary, top view of the electrode of FIG. 2.
Figure 6:
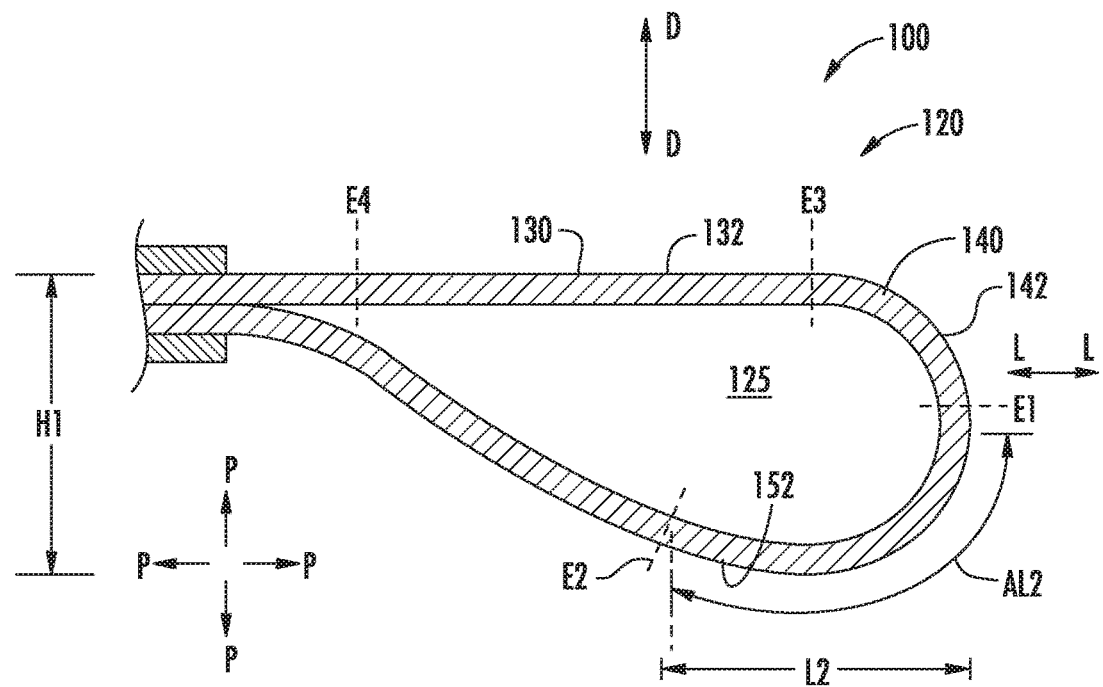
FIG. 6 is a fragmentary, cross-sectional view of the electrode of FIG. 2 taken along the line 6-6 of FIG. 5.
Figure 7:
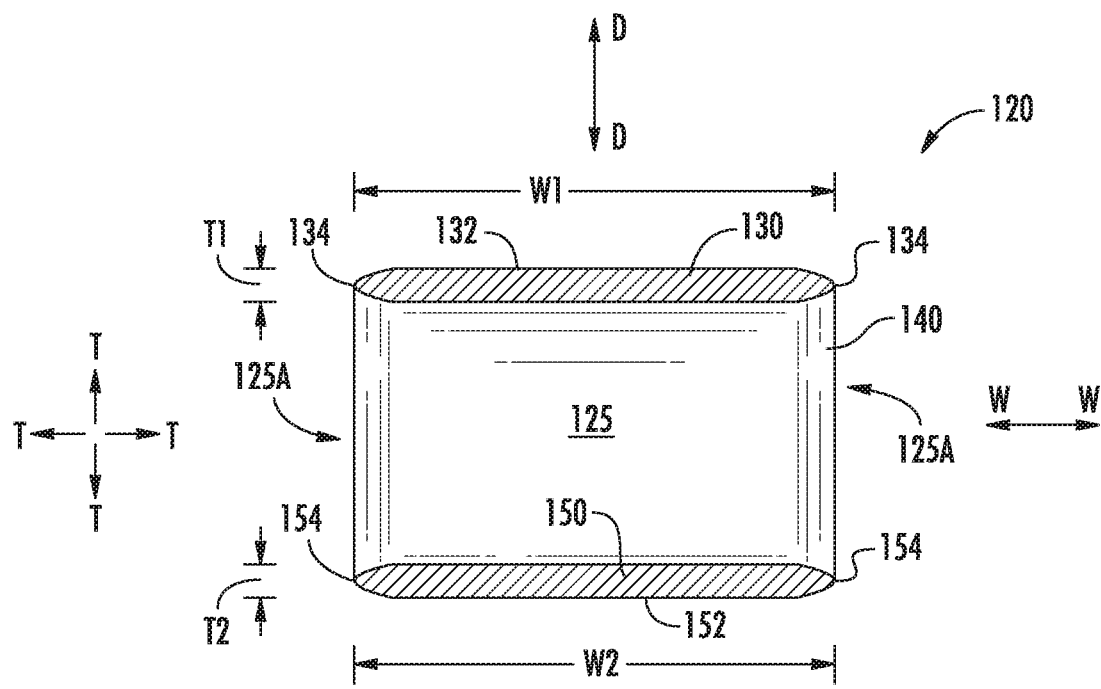
FIG. 7 is a cross-sectional view of the electrode of FIG. 2 taken along the line 7-7 of FIG. 5.

With reference to FIGS. 5-7, the working portion 120 has a primary or longitudinal axis L-L, a widthwise or first lateral axis W-W that is perpendicular to the longitudinal axis L-L, and a depthwise or second lateral axis D-D that is perpendicular to the longitudinal axis L-L and perpendicular to the first lateral axis W-W. The working portion 120 extends from a distal end 122A (FIG. 3) to an opposing proximal end 122B. The working portion 120 has an outer or top side 122C and an opposing patient facing or bottom side 122D.

The working portion 120 includes a thin band or strip 124 having opposed lateral edges 126. The strip 124 is configured to form or define a loop 128. In some embodiments and as shown, the loop 128 is generally tear drop-shaped in a cross-sectional profile plane P-P (FIGS. 5 and 6), the plane P-P being parallel to the longitudinal axis L-L and parallel to the depthwise axis D-D. In some embodiments and as shown, the loop 128 is generally tear drop-shaped in all planes parallel to the profile plane from lateral edge 126 to lateral edge 126.

The working portion 120 may be formed by any suitable technique. In some embodiments, the working portion 120 is formed by bending a metal part. In some embodiments, the strip 124 and the tail portion 114 are formed by flattening a portion of a metal rod (e.g., by drawing) to a prescribed width and then bending the strip 124 back into the shape of the loop 128.

In some embodiments, the lateral edges 126 or portions thereof are sharp. In some embodiments, one or both of the edges 126 is sharpened (e.g., by cutting, machining, extrusion, or casting) to a sharp edge. In some embodiments, the lateral edges 126 have substantially the same thickness as the remainder of the strip 124.

The working portion 120 includes a top wall 130, a bottom wall 150 and a transition wall 140 connecting the top wall 130 to the bottom wall 150. The working portion 120 is hollow so that the walls 130, 140, 150 collectively form a socket 125. The socket 125 extends laterally (substantially parallel to the axis W-W) and terminates at opposed openings 125A.

The top wall 130 includes a planar outer surface 132. The planar outer surface 132 extends lengthwise from a distal end E3 to a proximal end E4, and laterally from a first lateral edge 134 to an opposing, parallel lateral edge 134. In some embodiments, the top wall lateral edges 134 are sections of the strip lateral edges 126. According to some embodiments, the outer surface 132 is substantially continuous and substantially planar from end E3 to end E4 and edge 134 to edge 134.

In some embodiments, the planar outer surface 132 has a length L1 (FIG. 5) in the range of from about 6.5 mm to 11.5 mm.

In some embodiments, the planar outer surface 132 has a width W1 (FIG. 7) in the range of from about 1 mm to 4 mm.

In some embodiments, the planar outer surface 132 has an area in the range of from about 6.5 mm$^2$ to 48 mm$^2$.

In some embodiments, the top wall 130 has a thickness T1 (FIG. 7) in the range of from about 0.5 mm to 1.0 mm.

The bottom wall 150 is partially lobe-shaped. The bottom wall 150 has an outer contact surface 152. As discussed in more detail below, the bottom wall 150 and the contact surface 152 each have a rounded, curved or arcuate longitudinal profile, and a linear or flat widthwise profile.

The contact surface 152 extends lengthwise from a distal end E1 to a proximal end E2, and laterally from a first lateral edge 154 to an opposing, parallel lateral edge 154. In some embodiments, the contact surface lateral edges 154 are sections of the strip lateral edges 126. According to some embodiments, the contact surface 152 is substantially continuous from end E1 to end E2 and edge 154 to edge 154.

The contact surface 152 has a curved or arcuate shape and defines a curved contact surface profile in the profile plane P-P. In some embodiments and as shown, the contact surface 152 has the curved profile P in substantially all planes parallel to the profile plane P-P from lateral edge 154 to lateral edge 154 and from the end E1 to the end E2.

The curved profile P has an arc length AL2 (FIG. 6) extending from end E1 to end E2. The profile P is convex relative to the space below the bottom wall 150 and, when used to ablate by brushing, is convex relative to the surface of the tissue being treated. According to some embodiments, there are no sharp corners, sharp edges, hard angles or sharp transitions in the curve of the profile P. According to some embodiments, the profile P follows a smooth, continuous curve. In some embodiments, the profile P is a non-uniform curve.

In some embodiments, the profile P is or includes a truncated elliptical shape. In some embodiments, the profile P is or includes a partial cylindrical shape. In some embodiments, the profile P has a half heart curve shape.

In some embodiments, the minimum arc radius of the profile P is at least 1.5 mm. In some embodiments, the minimum arc radius of the profile P is in the range of from about 1.5 mm to 2.0 mm.

In some embodiments and as shown, the contact surface 152 is curved in the longitudinal direction and flat in the lateral direction from end E1 to E2. That is, the contact surface 152 is flat or planar in a cross-sectional transverse plane T-T (FIGS. 5 and 7) that is parallel to the widthwise axis W-W and the depthwise axis D-D. In some embodiments, the contact surface 152 is flat or planar in substantially all cross-sectional transverse planes parallel to cross-sectional transverse plane T-T from lateral edge 154 to lateral edge 154 and from the end E1 to the end E2.

According to some embodiments and as shown, there are no openings in the contact surface 152.

In some embodiments, the contact surface 152 has a linear length L2 (FIG. 6) in the range of from about 2 mm to 4 mm.

In some embodiments, the contact surface 152 has an arc length AL2 (FIG. 6) in the range of from about 3 mm to 5 mm.

In some embodiments, the contact surface 152 has a width W2 (FIG. 7) that is at least 1 mm and, in some embodiments, is in the range of from about 1 mm to 4 mm.

In some embodiments, the contact surface 152 has an area in the range of from about 1 mm$^2$ to 8 mm$^2$.

In some embodiments, the bottom wall 150 has a thickness T2 (FIG. 7) in the range of from about 0.5 mm to 1 mm.

The transition wall 140 connects the top wall 120 to the bottom wall 150 and extends between the planar outer surface 132 and the curved contact surface 152. In some embodiments, the outer surface 142 of the transition wall 140 has a curved or arcuate shape in the profile plane P-P. In some embodiments and as shown, the outer surface 142 has a curved profile in substantially all planes parallel to the profile plane P from lateral edge 126 to lateral edge 126. In some embodiments and as shown, the curved profile P of the outer surface 142 is convex. According to some embodiments, the curved profile P of the outer surface 142 is without sharp edges or transitions and follows a smooth, continuous curve. In some embodiments, the profile is or includes a truncated elliptical shape. In some embodiments, the profile is or includes a partial cylindrical shape.

In some embodiments and as shown, the outer surface 142 is curved in the longitudinal direction and flat in the lateral direction as discussed above with regard to the contact surface 152. That is, the outer surface 142 is flat or planar in the cross-sectional transverse plane T-T and, in some embodiments, is flat or planar in substantially all cross-sectional transverse planes parallel to cross-sectional transverse plane T-T from lateral edge 126 to lateral edge 126.

In some embodiments, the height distance H1 (FIG. 6) between the top wall surface 132 and the lowest point of the contact surface 152 is in the range of from about 2.5 mm to 3.5 mm.

In some embodiments, the socket 125 has a volume in the range of from about 7.1 mm$^3$ to 50.25 mm$^3$.

In some embodiments, the supplemental wiping insert 104 is a sponge or gauze. The supplemental wiping insert 104 may be disposable. In some embodiments, the insert 104 is formed of an electrically nonconductive material. In some embodiments, the insert 104 (e.g., sponge or gauze) is sized such that it can be inserted into the socket 125 with extension portions 104A of the insert 104 projecting outwardly through the openings 125A and beyond one or both of the lateral edges 126 a distance L3 (FIG. 4). In some embodiments, the distance L3 is in the range of from about 0 mm to 1 mm.

The electrode 100 may be formed by bending or otherwise forming a metal component into the shape of the electrode member 110 as described above. The insulation sleeve 102 is mounted around the shank 112 and the terminal end of the tail portion 114. For example, the insulation sleeve 102 may be heat-shrunk about the electrode member 110. Covering the tail portion 114 in this manner prevents the free end of the tail portion 114 from being exposed, where it may interfere with use of the electrode 100 (e.g., by catching on the patient or objects in the surgical field or the surgical table like gauze).

The system 10 and the electrode 100 may be used as follows in accordance with embodiments of the invention. The system 10 and the electrode 100 may be used to ablate tissue by vaporization in accordance with some method embodiments and the electrode 100 is especially well-suited to vaporize and ablate tissue in a controlled manner. The system 10 and the electrode 100 may be used to ablate skin tissue. The electrode 100 may be used to conduct cosmetic ablative procedures on skin tissue. The system 10 and the electrode 100 may also be used to scrape, cut, cauterize, coagulate, and/or desiccate tissue of a patient.

The electrode 100 may be used in different operational modes including a brushing mode, a cutting mode, a scraping mode, and a wiping mode.

In the brushing mode the electrode 100 is used to execute a brushing step, wherein an operator drags or slides the contact surface 152 of the working portion 120 in contact with and across an outer surface of tissue of a patient. As the electrode brushes across the tissue, it ablates a layer of the tissue.

Figure 8:
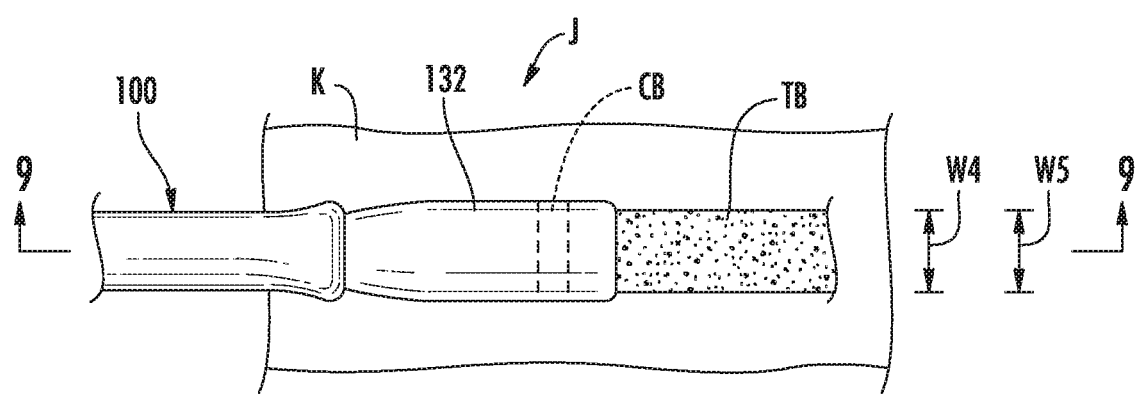
FIG. 8 is a fragmentary, top view of the system of FIG. 1 being used to execute a brushing step on a patient's tissue to form a treated band of tissue.
Figure 9:
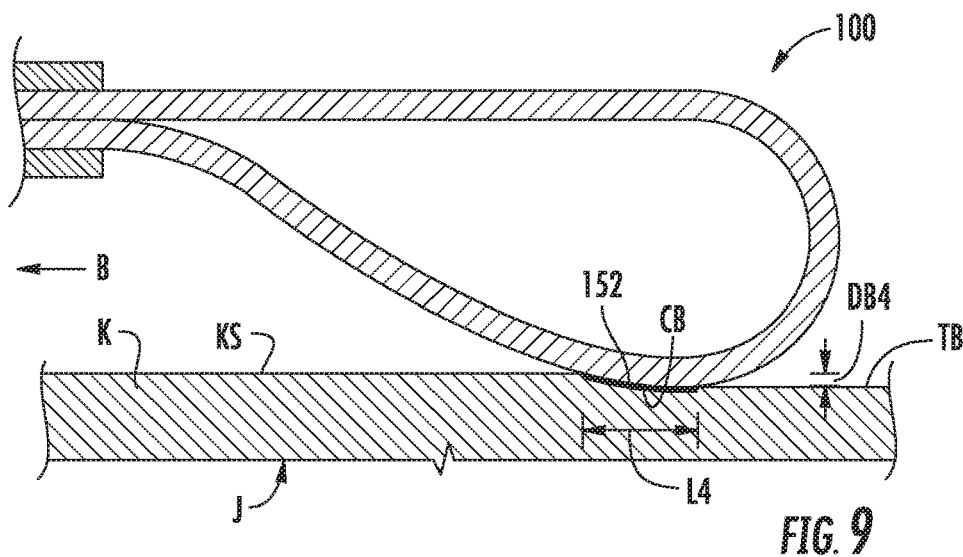
FIG. 9 is a fragmentary, cross-sectional view of the system and patient tissue of FIG. 8 taken along the line 9-9 of FIG. 8.

For example, FIGS. 8 and 9 illustrate the working portion 120 being slid or brushed across a surface KS of a surface tissue K of a patient J. The working portion 120 is placed in contact with the tissue surface K such that a contact band CB is formed. The contact band CB is the region of tissue K that is in contact with the contact surface 152 at any given time.

The contact surface 152 is maintained in contact with the tissue surface K while the contact surface 152 is displaced or wiped across the tissue K in a direction B. Simultaneously with the brushing movement, the electrosurgical apparatus 20 is operated to deliver RF energy to the contact surface 152 as discussed above. Displacing the electrode 100 in this manner progressively advances the contact band CB to thereby create a broad swath or treated band TB of treated tissue. In some embodiments, the electrode vaporizes and ablates the tissue in the contact band CB, so that the brushing step vaporizes and ablates a broad band of a layer of tissue and the treated band TB is tissue from which overlying tissue has been vaporized and ablated.

The broad width of the contact band CB facilitates quicker surgical times. In some embodiments, substantially the entire area of the tissue within the treated band TB is ablated by the brush stroke.

In some embodiments, the depth DB4 (FIG. 9) of ablation across the width of the treated band TB is substantially uniform.

In some embodiments, the procedure includes executing a plurality of light pressure brush strokes over the tissue to create a controlled and uniform depth of tissue removal by ablation. The electrode 100 can be brushed in both the direction B and the opposite direction.

The broad line of contact (i.e., the contact band CB) distributes the energy from the apparatus 20 over a greater area, which may decrease undesired damage to collateral tissues.

In some embodiments, the CB has a width W4 (FIG. 8; transverse to the brush stroke direction B) that is greater that its length L4 (FIG. 9; generally parallel to the direction B). In some embodiments, the ratio of the width W4 to the length L4 is in the range of from about 1 mm to 2 mm.

The length L4 of the contact band CB may be a function of the pressure applied to the tissue by the electrode 100 and/or the location of the contact band CB on the profile of the contact surface 152. Thus, the length L4 of the contact band CB may vary between a thin line to a thick line or band extending across the width of the treated band TB. In some embodiments, the length L4 is in the range of from about 1 mm to 3 mm, in some embodiments is in the range of from about 1 mm to 2 mm, and, in some embodiments, is in the range of from about 2 mm to 3 mm.

In some embodiments, the width W4 of the contact band CB is in the range of from about 1 mm to 4 mm. In some embodiments, the width W4 is substantially the same as the width W2 of the contact surface 152. In some embodiments, the width W4 is substantially the same as the width W5 (FIG. 8) of the treated band TB.

As discussed above, in some embodiments, throughout the brushing step or stroke the electrode contact surface 152 applies only a light load or pressure onto the tissue to be ablated.

According to some embodiments, the electrode 100 does not cut tissue during the brushing step.

The contact band CB is tangential to the curve of the profile P. The smooth, continuous shape of the contact surface 152 and the contact band CB facilitates minimal drag resistance between the electrode 100 and the tissue for quick, precise execution of procedures (especially ablative procedures).

The broad width W4 of the contact band CB and the geometry of the contact surface 152 (i.e., the smooth, gradual curvature of the curved profile P) reduce the depth of entry or embedding of the electrode 100 into the tissue for a given pressure of working portion 120 onto the tissue K. This enables the operator to more easily and accurately modulate or control the depth of entry into the tissue. As a result, the operator can more effectively and reliably prevent the working portion 120 from cutting the tissue when cutting is not desired. The operator can better control the depth of treatment of the tissue by ohmic heating. The operator can better limit ablation of the tissue to a shallow depth, if desired.

During the brushing step, the operator can gauge the position of one of the lateral edges 126 of the contact surface 152 by visually observing and monitoring the opposite parallel lateral edge 126. Each of the parallel lateral edges 126 can thereby serve as a lateral field spatial reference for the other to enable the operator to better ascertain and track the position of the contact surface lateral edges 154, and thus the contact band CB, relative to the patient. This feature can be particularly advantageous when one of the lateral edges 126 of the working portion 120 is obscured (e.g., by the patient's anatomy or equipment). The parallel lateral edges 126 allow the operator to have spatial awareness and navigate demarcated regions to prevent collateral tissue damage.

During the brushing step, the operator can also gauge the depthwise position of the contact surface 152 by visually observing and monitoring the planar top wall surface 132, which is disposed a fixed distance above and overlying the contact surface 152 when the top wall surface 132 is substantially parallel to the tissue being ablated. The surface 132 can thereby serve as a depth field spatial reference to enable the operator to better ascertain and track the depth position of the contact surface 152, and thus the contact band CB, relative to the patient. This feature can be particularly advantageous when the operator wants to carefully limit the depth of entry of the contact surface 152 into the tissue.

In the cutting mode, the electrode 100 is used to execute a cutting step wherein it cuts (and, in some cases, coagulates) tissue of the patient. Either or both of the lateral edges 126 can be used to cut the tissue. The electrode 100 can be used to electrosurgically cut tissue with the electrosurgical apparatus 20 operated to deliver RF energy to the contact surface 152 as discussed above. The electrode 100 can be used to cut tissue while non-energized.

In the scraping mode, the electrode 100 is used to execute a tissue scraping step. Either or both of the lateral edges 126 can be used to scrape the tissue. In some embodiments, the electrode 100 is used to scrape tissue with the electrode non-energized (i.e., without the electrosurgical apparatus 20 operated to deliver RF energy to the contact surface 152 as discussed above). However, in other embodiments, the electrode 100 may be energized during scraping.

The scraping step may be employed to remove tissue residue that has been volatized, desiccated, coagulated or otherwise treated by a brushing step or cutting step as described above. The provision of scraping edges 126 on the brushing electrode 100 relieves the operator of the need to exchange the brush electrode 100 for another instrument, and can thereby increase the safety of the patient by reducing surgical time.

In the wiping mode, the electrode 100 is used to execute a wiping step to remove tissue from the surgical region. In the wiping mode, the insert 104 is mounted in the socket 125 as shown in FIGS. 3 and 4. The extensions 104A are then used to wipe material from the tissue of the patient. Typically, the electrode 100 is used to wipe tissue with the electrode 100 non-energized.

In some embodiments, the wiping step is employed to remove tissue residue that has been volatized, desiccated, coagulated, cut or scraped by a brushing step, cutting step or scraping step as described above. The provision of the wiping insert 104 on the brushing electrode 100 relieves the operator of the need to exchange the brush electrode 100 for another instrument, and can thereby increase the safety of the patient by reducing surgical time.

In some embodiments, the system 10 includes a plurality of electrodes 100 of different shapes and/or sizes to permit the operator to customize the system to the treatment, patient, or surgical step at hand.

In some embodiments, the socket 125 may be omitted or filled with an electrically conductive or nonconductive material. For example, the working portion 120 may be solid (i.e., void free).

Portions of the electrode 100 may be bendable to customize the shape or angle of the electrode 100 to permit the operator to customize the system to the treatment, patient, or surgical step at hand. For example, the working portion 120 and/or the shank 112 may be malleable. The electrode 100 may be bent into or supplied in different configurations to provide access to challenging spaces. Methods of using the system and electrode may include bending the electrode prior to use or between steps.

The system 10 and the electrode 100 may be used as follows in accordance with embodiments of the invention to execute dental gum treatments. The system 10 and the electrode 100 may be used to ablate gum tissue by vaporization. In some embodiments, the electrode 100 is used to ablate a layer offending gum tissue to effect a cosmetic treatment.

Figure 10:
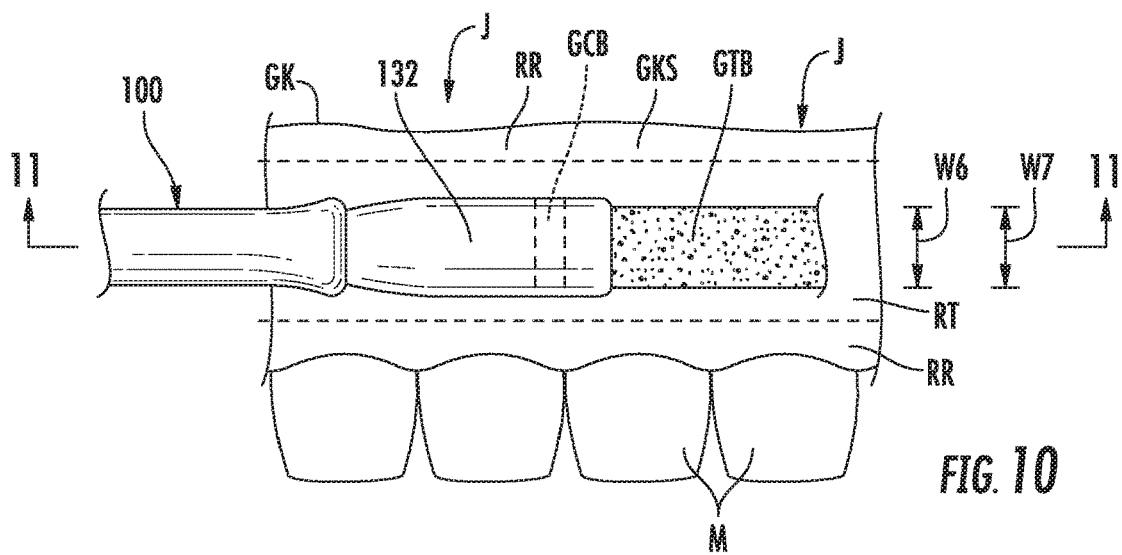
FIG. 10 is a fragmentary, top view of the system of FIG. 1 being used to execute a brushing step on a patient's gum tissue to form a treated band of gum tissue.
Figure 11:
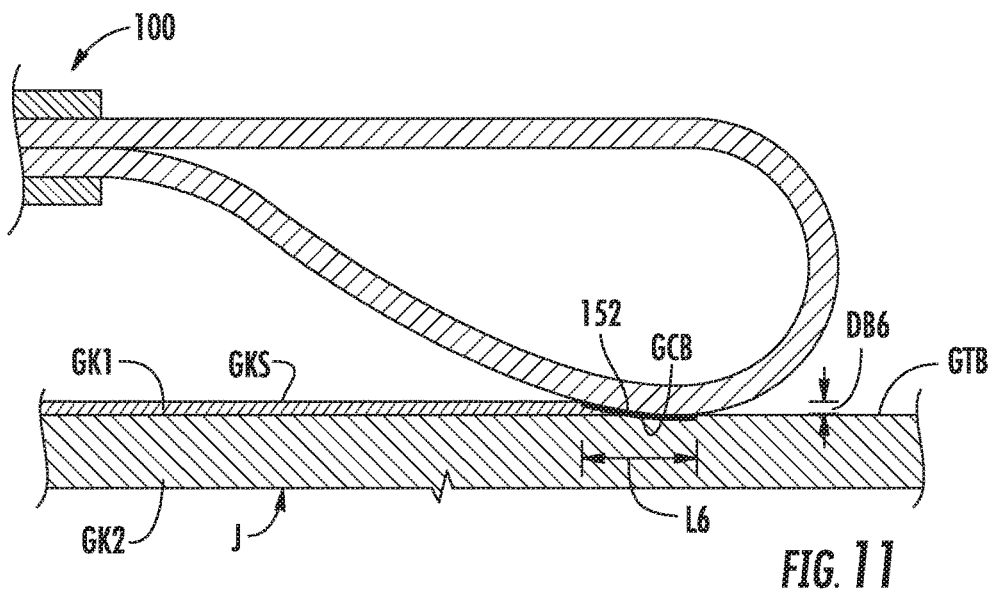
FIG. 11 is a fragmentary, cross-sectional view of the system and patient tissue of FIG. 10 taken along the line 11-11 of FIG. 10.

With reference to FIGS. 10 and 11, the electrode 100 is used in the brushing mode to vaporize and ablate a surface layer GK1 of a gum tissue GK of a patient J. In the brushing mode, the operator drags or slides the contact surface 152 of the working portion 120 in contact with and across an outer surface of the gum tissue GK of the patient in the manner described above with reference to FIGS. 8 and 9.

For example, FIGS. 10 and 11 illustrate the working portion 120 being slid or brushed across a surface GKS of the gum tissue GK. The patient's teeth M are also illustrated. The working portion 120 is placed in contact with the tissue surface GKS such that a contact band CB is formed. The contact surface 152 is maintained in contact with the tissue surface GKS while the contact surface 152 is displaced or wiped across the gum tissue GK in a direction B. Simultaneously with the brushing movement, the electrosurgical apparatus 20 is operated to deliver RF energy to the contact surface 152 as discussed above. In this manner, the contact band GCB is progressively advanced to thereby create a broad swath or treated band GTB of treated gum tissue. The electrode 100 vaporizes and ablates the gum tissue in the contact band GCB, so that the brushing step vaporizes and ablates a broad band of gum tissue and the treated band GTB is gum tissue from which overlying tissue has been vaporized and ablated. Tissue in the treated band GTB may be killed but not ablated, as well.

According to some embodiments, with reference to FIG. 11, the brushing step ablates and/or kills an epithelium layer GK1 of the patient's gum tissue while leaving an underlying connective tissue layer GK2 substantially unaffected, undamaged or minimally damaged by ablation or heat. In some embodiments, the depth of ablation DB6 (FIG. 11) created by the brushing step is less than 0.01 mm and, in some embodiments, is in the range of from about 0.01 mm to 0.15 mm. According to some embodiments, the depth of ablation DB6 is substantially uniform across the width of the treated band GTB. In some embodiments, the width W6 (FIG. 10) of the contact band GCB is greater than the length L6 (FIG. 11) of the contact band GCB. In some embodiments, the ratio of the width W6 to the length L6 is in the range of from about 1 mm to 2 mm.

As discussed above, the length L4 of the contact band GCB may be a function of the pressure applied to the tissue. In some embodiments, the length L4 is in the range of from about 0.5 mm to 2 mm, in some embodiments is in the range of from about 0.5 mm to 1 mm, and, in some embodiments, is in the range of from about 1 mm to 2 mm.

In some embodiments, the width W6 (FIG. 10) of the contact band GCB is in the range of from about 1 mm to 4 mm. In some embodiments, the width W6 is substantially the same as the width W2 of the contact surface 152. In some embodiments, the width W6 is substantially the same as the width W7 (FIG. 10) of the treated band GTB.

In some embodiments, the electrode 100 is used to treat gingival hyperplasia.

In some embodiments, the electrode 100 is used to treat racial pigmentation. The electrode may be used to treat both gingival hyperplasia and racial pigmentation in the same procedure.

As discussed above, in some embodiments, throughout the brushing step or stroke the electrode contact surface 152 applied only a light load or pressure onto the gum tissue to be ablated.

The smooth curved profile of the contact surface 152 enables the electrode 100 to slide smoothly across the tissue as it ablates. According to some embodiments, the electrode 100 does not cut gum tissue during the brushing step.

The broad width W4 of the contact band CB and the geometry of the contact surface 152 (i.e., the smooth, gradual curvature of the curved profile P) reduce the depth of entry or embedding of the electrode 100 into the tissue for a given pressure of working portion 120 onto the gum tissue GK. This enables the operator to more easily and accurately modulate or control the depth of entry into the gum tissue. As a result, the operator can more effectively and reliably prevent the working portion 120 from cutting the gum tissue when cutting is not desired. The operator can better control the depth of treatment of the gum tissue by ohmic heating. The operator can better limit ablation of the gum tissue to a shallow depth, if desired.

During the brush step, the operator can gauge the position of one of the lateral edges 126 of the contact surface 152 by visually observing and monitoring the opposing parallel lateral edge 126 as described above. In particular, an exposed parallel lateral edge 126 can be used as a lateral field spatial reference for the other to enable the operator to better ascertain and track the position of an obscured lateral edge relative to a restricted region RR (demarcated in FIG. 10 by dashed lines). The restricted region RR may be gum tissue that should not be ablated ("non-offending tissue") such as tissue proximate the lip line. The lateral edge 126 of the electrode proximate the restricted region may be obscured by the patient's lip.

During the brushing step, the operator can also gauge the depthwise position of the contact surface 152 by visually observing and monitoring the planar top wall surface 132, which is disposed a fixed distance above and overlying the contact surface 152 when the top wall surface 132 is substantially parallel to the tissue being ablated, as discussed above. The surface 132 can thereby serve as a depth field spatial reference to enable the operator to better ascertain and track the depth position of the contact surface 152 into the patient's gum tissue GK. This feature can be particularly advantageous when the operator wants to carefully limit the depth of entry of the contact surface 152 into the gum tissue.

Following the brushing step, the operator may cut and/or scrape gum tissue from the treated band using the cutting mode and/or the scraping mode as discussed above. Gum tissue may be cut or scraped from the treated region using either or both of the lateral edges 126. The electrode 100 can be used to cut and/or scrape tissue either with or without the electrosurgical apparatus 20 operated to deliver RF energy to the contact surface 152 as discussed above. In some embodiments, the electrode 100 is used to scrape gum tissue without the electrosurgical apparatus 20 operated to deliver RF energy to the contact surface 152 in order to avoid unintended damage to the underlying tissue. In some embodiments, in the scraping step, a lateral edge 126 is used to scrape away or remove tissue that has been coagulated by the ablation step, such as collagen from the treated gum tissue that has become gelatinized.

In some embodiments, the system 10 and electrode 100 are operated in a wiping mode to remove gum tissue from the surgical region using the insert 104 (or other insert) mounted in the socket 125, as discussed above. The extensions 104A may be used to wipe ablated, coagulated or otherwise loosened gum tissue from the patient. Typically, the electrode 100 is used to wipe tissue with the electrode 100 non-energized. In particular, the wiping step may be employed to remove gum tissue that has been desiccated, coagulated, cut or scraped by the gum brushing step and the gum scraping step as described above. In some embodiments, in the wiping step, the insert 104 is used to wipe away or remove tissue that has been coagulated by the ablation step, such as collagen from the treated gum tissue that has become gelatinized.

The operator may make multiple brush strokes with the electrode 100 as needed to ablate a desired region of the gum tissue. For example, the operator may continue to brush a target region RT (demarcated by dashed lines in FIG. 10) of tissue ("offending tissue") bounded by restricted regions RR of tissue ("non-offending tissue") until most or substantially all of the target region RT has been ablated as described. Scraping and wiping steps as described above may be executed between brush strokes to remove residual tissue in order to clear the surgical field for further ablation or inspection. The operator may alternate between the brushing, scraping and wiping steps as needed to progressively ablate and clear the target region RT.

For example, in procedures according to some embodiments, the operator uses the brushing, scraping and wiping steps and techniques described above as follows:

a) The operator prepares the system 10, including installing the electrode 100 in the handpiece 30;

b) With the electrode 100 energized, the operator brushes surface gum tissue in the target region RT with the contact surface 152 to thereby vaporize and ablate the contacted tissue. The operator may take care not to unintentionally contact and ablate tissue in the restricted regions RR by monitoring the position of the working portion 120 using visual observation of the lateral edges 126, as discussed above. The operator may control the depth of ablation using visual observation of the planar surface 132, as discussed above;

c) With the electrode 100 de-energized, the operator scrapes volatilized residual tissue from the ablative process (e.g., coagulated collagen or other tissue) from the target region RT using the edges 126, as described above;

d) With the electrode 100 de-energized, the operator inserts the wiping insert 104 into the socket 125 and wipes volatilized residual tissue from the ablative process from the target region RT using the end sections 104A, as described above. The wiped residual tissue may include residual tissue loosened by the scraping step;

e) The procedure may include executing a plurality of brush strokes over the gum tissue to create a controlled and uniform depth of gum tissue removal by ablation. The operator can brush the electrode 100 in both the direction B and the opposite direction. The operator may repeat steps a), b) and c) as needed to progressively ablate and clear the target region RT. The operator may remove the dirtied wiping insert 104 from the electrode and replace it with a new, clean wiping insert 104 to use in subsequent wiping steps.

The electrode 100 can be used to conduct cosmetic ablative procedures on the gums. According to some embodiments, the electrode 100 and the electrosurgical gum treatment methods described above are used to treat gingival hyperplasia. In this condition, the patient has an excess of gingival tissue growth and discoloration of the gums. The brushing step is used to ablate the epithelium layer (corresponding to layer GK1), and the scraping and wiping steps are used to remove the remaining residual tissue from the ablation.

The electrode 100 can be used to conduct cosmetic ablative procedures on the gums. According to some embodiments, the electrode 100 and the electrosurgical gum treatment methods described above are used to treat racial pigmentation. In this condition, the patient has uneven or undesirably dark coloration of the gums. The brushing step is used to ablate the epithelium layer (corresponding to layer GK1), and the scraping and wiping steps are used to remove the remaining residual tissue from the ablation.

The system 10 may further include a family or set of a plurality of brush electrodes 100 of different widths. The operator can then select the brush electrode or electrodes from the set having the desired width(s) for the intended procedure. For example, the width of electrode may be chosen dependent on the constraints of the surgery.

Electrodes according to embodiments of the present invention can overcome various problems that may otherwise be encountered when electrodes of known shapes (e.g., spherical ball electrodes) are pressed into service to ablate tissue. As compared to such known electrodes, electrodes of the present invention can provide shorter surgical times, more complete removal of offending tissue, more even depth of tissue removal, reduced heat transfer (which may cause undesirable tissue damage) to the tissue, improved visualization of the surgical field, and an overall better aesthetic outcome.

Systems and methods as disclosed herein can enable an operator (e.g., a physician) to efficiently and precisely perform ablative treatments with less time, less cost, fewer follow-up procedures, less collateral tissue damage, and less bleeding compared to known electrosurgery apparatus and procedures. For example, while it is known to ablate gum tissue by contacting a sphere electrode with gum tissue in a repeated "pecking" motion, the pecking method is slow and imprecise, leading to numerous drawbacks in execution and result.

In some embodiments, at least the working portion 120 of the electrode member 110 is formed of a metal core (e.g., brass or molybdenum) surrounded by a cladding (e.g., a silver alloy). Suitable materials of this type are disclosed in U.S. Published Patent Application No. 2007/0055226, the disclosure of which is incorporated herein by reference. A cladding of silver alloy can provide less surface damage, less pain and suffering, faster healing time, and a smoother brush stroke with less coagulative tissue clinging to the working portion 120 and obscuring the surgical field.

Many alterations and modifications may be made by those having ordinary skill in the art, given the benefit of present disclosure, without departing from the spirit and scope of the invention. Therefore, it must be understood that the illustrated embodiments have been set forth only for the purposes of example, and that it should not be taken as limiting the invention as defined by the following claims. The following claims, therefore, are to be read to include not only the combination of elements which are literally set forth but all equivalent elements for performing substantially the same function in substantially the same way to obtain substantially the same result. The claims are thus to be understood to include what is specifically illustrated and described above, what is conceptually equivalent, and also what incorporates the essential idea of the invention.

What is claimed:

1. A method for treating gum tissue of a patient, the method comprising:
   providing an electrode having a contact surface, wherein the contact surface has a curved profile;
   placing the contact surface in contact with an outer surface of the gum tissue of the patient; and
   sliding the contact surface across and in contact with the outer surface of the gum tissue while applying electrosurgical currents to the gum tissue via the contact surface to thereby vaporize and ablate at least a portion of the gum tissue and form a treated band of the gum tissue;
   wherein:
      the curved profile of the contact surface extends along a first axis;
      the contact surface has a linear profile along a second axis perpendicular to the first axis; and
      the step of sliding the contact surface across and in contact with the outer surface of the gum tissue includes sliding the contact surface across and in contact with the outer surface of the gum tissue in a direction substantially parallel to the first axis while applying the electrosurgical currents to the gum tissue via the contact surface to thereby vaporize and ablate at least a portion of the gum tissue.

2. The method of claim 1 wherein the curved profile has a minimum arc radius of at least 1.5 mm.

3. The method of claim 1 wherein:
   the step of sliding the contact surface across and in contact with the outer surface of the gum tissue includes sliding the contact surface across and in contact with the outer surface of the gum tissue in a brushing direction while applying electrosurgical currents to the gum tissue via the contact surface to thereby vaporize and ablate at least a portion of the gum tissue;
   an engagement interface between the contact surface and the outer surface of the gum tissue defines a contact band having a first dimension parallel to the brushing direction and a second dimension perpendicular to the first dimension; and
   the second dimension is greater than the first dimension.

4. The method of claim 3 wherein:
   the first dimension is in the range of from about 0.5 mm to 2 mm; and
   the second dimension is in the range of from about 1 mm to 4 mm.

5. The method of claim 1 wherein the step of sliding the contact surface across and in contact with the outer surface of the gum tissue includes ablating at least a portion of the gum tissue without cutting the gum tissue.

6. The method of claim 1 wherein:
the electrode further includes a lateral edge; and
the method further includes scraping residual tissue from the treated band using the lateral edge.

7. The method of claim 1 further including:
mounting a wiping insert on the electrode; and
wiping residual tissue away from the treated band using the wiping insert mounted on the electrode.

8. The method of claim 1 wherein:
the electrode includes first and second opposed lateral edges; and
the method includes monitoring the first lateral edge to determine a location of the second lateral edge relative to the patient's gum.

9. The method of claim 1 wherein:
the electrode includes a bottom wall and a top wall overlying the bottom wall;
the contact surface is on the bottom wall;
the top wall includes a planar surface overlying the contact surface; and
the method includes monitoring the planar surface to determine a depthwise location of the contact surface relative to the gum tissue.

10. The method of claim 1 including:
providing an electrode set including a plurality of electrodes having contact surfaces of different widths from one another, each of the electrodes having a curved profile; and
selecting the electrode from the set of electrodes.

11. The method of claim 1 including using the electrode to ablate the gum tissue to a depth in the range of from about 0.01 mm to 0.15 mm in the treated band.

12. The method of claim 1 including using the electrode to ablate an epithelium layer of the gum tissue while leaving an underlying connective tissue layer substantially undamaged in the treated band.

13. The method of claim 1 wherein the step of sliding the contact surface across and in contact with the outer surface of the gum tissue while applying electrosurgical currents to the gum tissue via the contact surface removes gingiva hyperplasia from the patient's gums.

14. The method of claim 1 wherein the step of sliding the contact surface across and in contact with the outer surface of the gum tissue while applying electrosurgical currents to the gum tissue via the contact surface removes racial pigmentation from the patient's gums.

15. The method of claim 1 wherein the electrode is affixed to a handle.

16. The method of claim 1 wherein the step of sliding the contact surface across and in contact with the outer surface of the gum tissue includes ablating the gum tissue such that a depth of ablation across a width of the treated band of the gum tissue is substantially uniform.

\* \* \* \* \*